(12) United States Patent
Wang et al.

(10) Patent No.: US 10,471,195 B2
(45) Date of Patent: *Nov. 12, 2019

(54) USER INTERFACES FOR DIALYSIS DEVICES

(71) Applicant: Fresenius Medical Care Holdings, Inc., Waltham, MA (US)

(72) Inventors: Fei Wang, Concord, CA (US); Martin Joseph Crnkovich, Walnut Creek, CA (US); Roland Levin, San Ramon, CA (US); Michael Emmanuel Kotsos, Walnut Creek, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 33 days.

This patent is subject to a terminal disclaimer.

(21) Appl. No.: 15/692,172

(22) Filed: Aug. 31, 2017

(65) Prior Publication Data

US 2017/0361005 A1 Dec. 21, 2017

Related U.S. Application Data

(63) Continuation of application No. 15/198,465, filed on Jun. 30, 2016, now Pat. No. 9,775,937, which is a
(Continued)

(51) Int. Cl.
*G06F 19/00* (2018.01)
*G09G 5/14* (2006.01)
(Continued)

(52) U.S. Cl.
CPC ............ *A61M 1/1601* (2014.02); *A61M 1/16* (2013.01); *A61M 1/28* (2013.01); *G06F 3/0481* (2013.01);
(Continued)

(58) Field of Classification Search
CPC ........ A61M 1/16; A61M 1/1601; A61M 1/28; A61M 2205/3553; A61M 2205/3576;
(Continued)

(56) References Cited

U.S. PATENT DOCUMENTS 5,324,422 A 6/1994 Colleran et al.
5,421,823 A 6/1995 Kamen et al.
(Continued)

FOREIGN PATENT DOCUMENTS

DE 10-2005-025516 12/2006
WO 2006131775 12/2006
(Continued)

OTHER PUBLICATIONS

Heitmeier et al., "Sicherheitstechnik bei einem mikroprozessorgesteuerten Hämodialysegerät," Medizintechnik, vol. 105, pp. 118-124 (Apr. 1985), translation provided.
(Continued)

*Primary Examiner* — Afroza Chowdhury
(74) *Attorney, Agent, or Firm* — Fish & Richardson, P.C.

(57) ABSTRACT

In general, a dialysis device includes a first processing device for monitoring dialysis functions of the dialysis device, a second processing device, a display device, and memory. The memory is configured to store instructions that, when executed, cause the dialysis device to provide, on the display device, a first display region and a second display region, where the first display region is associated with the first processing device and the second display region is associated with the second processing device. At least a portion of the first display region cannot be obscured by the second display region.

31 Claims, 5 Drawing Sheets

Related U.S. Application Data continuation of application No. 12/971,335, filed on Dec. 17, 2010, now Pat. No. 9,408,958.

(51) Int. Cl.
| | |
|---|---|
| *G06F 3/0481* | (2013.01) |
| *A61M 1/16* | (2006.01) |
| *A61M 1/28* | (2006.01) |
| *G06F 3/0484* | (2013.01) |
| *G09G 5/12* | (2006.01) |

(52) U.S. Cl.
CPC ........ *G06F 3/0484* (2013.01); *G06F 19/3481* (2013.01); *G09G 5/12* (2013.01); *G09G 5/14* (2013.01); *A61M 2205/3553* (2013.01); *A61M 2205/3576* (2013.01); *A61M 2205/3584* (2013.01); *A61M 2205/502* (2013.01); *A61M 2205/505* (2013.01); *A61M 2205/52* (2013.01); *G09G 2370/16* (2013.01)

(58) Field of Classification Search
CPC .... A61M 2205/3584; A61M 2205/502; A61M 2205/505; A61M 2205/52; G06F 19/3481; G06F 3/0481; G06F 3/0484; G09G 2370/16; G09G 5/12; G09G 5/14; G16H 10/60; G16H 20/40; G16H 40/63
See application file for complete search history.

(56) References Cited

U.S. PATENT DOCUMENTS

| | | | |
|---|---|---|---|
| 5,431,626 A | 7/1995 | Bryant et al. | |
| 5,438,510 A | 8/1995 | Bryant et al. | |
| 5,492,125 A | 2/1996 | Kim et al. | |
| 5,788,851 A | 8/1998 | Kenley et al. | |
| 5,903,211 A | 5/1999 | Flego et al. | |
| 6,146,523 A | 11/2000 | Kenley et al. | |
| 6,503,062 B1 | 1/2003 | Gray et al. | |
| 6,699,188 B2 | 3/2004 | Wessel | |
| 6,808,369 B2 | 10/2004 | Gray et al. | |
| 6,814,547 B2 | 11/2004 | Childers et al. | |
| 6,929,751 B2 | 8/2005 | Bowman, Jr. et al. | |
| 7,082,106 B2 | 7/2006 | Sharma et al. | |
| 7,083,719 B2 | 8/2006 | Bowman, Jr. et al. | |
| 7,720,143 B2 | 5/2010 | Ichihashi et al. | |
| 7,779,365 B2 | 8/2010 | Fujita | |
| 8,075,509 B2 | 12/2011 | Molducci et al. | |
| 8,181,118 B2 | 5/2012 | Potts et al. | |
| 8,321,044 B2 | 11/2012 | Plahey et al. | |
| 8,992,777 B2 * | 3/2015 | Doyle | B01D 61/32 210/646 |
| 9,408,958 B2 | 8/2016 | Wang | |
| 9,775,937 B2 | 10/2017 | Wang et al. | |
| 2002/0196369 A1 | 12/2002 | Rieder et al. | |
| 2003/0050537 A1 | 3/2003 | Wessel | |
| 2003/0100963 A1 | 5/2003 | Potts et al. | |
| 2006/0250645 A1 | 11/2006 | Miyazaki | |
| 2007/0112603 A1 | 5/2007 | Kauthen et al. | |
| 2007/0156457 A1 | 7/2007 | Brown | |
| 2007/0216700 A1 | 9/2007 | Chen et al. | |
| 2008/0246377 A1 | 10/2008 | Molducci et al. | |
| 2009/0222119 A1 | 9/2009 | Plahey et al. | |
| 2010/0049114 A1 | 2/2010 | Brown et al. | |
| 2010/0137693 A1 | 6/2010 | Porras et al. | |
| 2010/0321324 A1 | 12/2010 | Fukai et al. | |
| 2011/0279389 A1 | 11/2011 | Yamazoe | |
| 2012/0154264 A1 | 6/2012 | Wang et al. | |
| 2016/0310653 A1 | 10/2016 | Wang et al. | |

FOREIGN PATENT DOCUMENTS

| | | |
|---|---|---|
| WO | 2007053683 | 5/2007 |
| WO | 2009122277 | 10/2009 |

OTHER PUBLICATIONS

Newton IQ Cycler Operator Manual, Part No. 470203 Rev. F, 2000-2006.

* cited by examiner

USER INTERFACES FOR DIALYSIS DEVICES

CROSS-REFERENCE TO RELATED APPLICATION

This application is a continuation and claims the priority of U.S. Ser. No. 15/198,465, filed Jun. 30, 2016, which is a continuation of U.S. Ser. No. 12/971,335, filed Dec. 17, 2010, now U.S. Pat. No. 9,408,958, issued on Aug. 9, 2016, the entire contents of each of which are hereby incorporated by reference.

TECHNICAL FIELD

This patent application relates generally to user interfaces for dialysis devices.

BACKGROUND

Dialysis is a treatment used to support a patient with insufficient renal function. The two principal dialysis methods are hemodialysis and peritoneal dialysis.

During hemodialysis ("HD"), the patient's blood is passed through a dialyzer of a dialysis machine while also passing a dialysis solution or dialysate through the dialyzer. A semi-permeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

During peritoneal dialysis ("PD"), a patient's peritoneal cavity is periodically infused with dialysis solution or dialysate. The membranous lining of the patient's peritoneum acts as a natural semi-permeable membrane that allows diffusion and osmosis exchanges to take place between the solution and the blood stream. These exchanges across the patient's peritoneum, like the continuous exchange across the dialyzer in HD, result in the removal waste products, including solutes like urea and creatinine, from the blood, and regulate the levels of other substances, such as sodium and water, in the blood.

Many PD machines are designed to automatically infuse, dwell, and drain dialysate to and from the patient's peritoneal cavity. The treatment typically lasts for several hours, often beginning with an initial drain cycle to empty the peritoneal cavity of used or spent dialysate. The sequence then proceeds through the succession of fill, dwell, and drain phases that follow one after the other. Each phase is called a cycle.

SUMMARY

In one aspect, a dialysis device includes a first processing device for monitoring dialysis functions of the dialysis device, a second processing device, a display device, and memory. The memory is configured to store instructions that, when executed, cause the dialysis device to provide, on the display device, a first display region and a second display region, where the first display region is associated with the first processing device and the second display region is associated with the second processing device. At least a portion of the first display region cannot be obscured by the second display region.

In another aspect, a method includes providing, on a display device associated with a dialysis machine, a first display region and a second display region, where the first display region is associated with a first processing device of the dialysis machine and the second display region is associated with a second processing device of the dialysis machine. The method further includes preventing at least a portion of the first display region from being obscured by the second display region.

In a further aspect, a method of providing dialysis treatment includes providing, on a display device associated with a dialysis machine during dialysis treatment of a patient, a first display region and a second display region. The first display region is associated with a first processing device of the dialysis machine and the second display region is associated with a second processing device of the dialysis machine. At least a portion of the first display region is prevented from being obscured by the second display region. The first display region is configured to present information about the dialysis treatment and the second region is configured to present one or more medical records associated with the patient.

Implementations can include one or more of the following features.

At a given point in time, only one of the first display region and the second display region can respond to input received from an input device.

The first display region includes information associated with a dialysis treatment session.

The first display region includes one or more notifications associated with a dialysis treatment session.

The second display region includes information associated with one or more medical records.

The instructions further cause the dialysis device to designate either the first display region or the second display region as an active display region.

Designating either the first display region or the second display region as an active display region includes designating, for a given point in time, which of the first display region and the second display region can respond to input received from an input device.

The dialysis device is configured to automatically designate the first display region as the active display region in response to a predetermined event.

The predetermined event includes one or more notifications associated with a dialysis treatment session.

The first display region and the second display region include a first viewing pane and a second viewing pane, respectively.

The dialysis device is configured to present the first display region and the second display region in a first dedicated display region of the display device and a second dedicated display region of the display device, respectively.

The dialysis device is configured to simultaneously present the first display region in the first dedicated display region and the second display region in the second dedicated display region.

The first dedicated display region and the second dedicated display region are arranged side by side.

Other aspects, features, and advantages will be apparent from the description and drawings, and from the claims.

BRIEF DESCRIPTION OF THE DRAWINGS

Like reference symbols in the various drawings indicate like elements.

DETAILED DESCRIPTION

Figure 1:
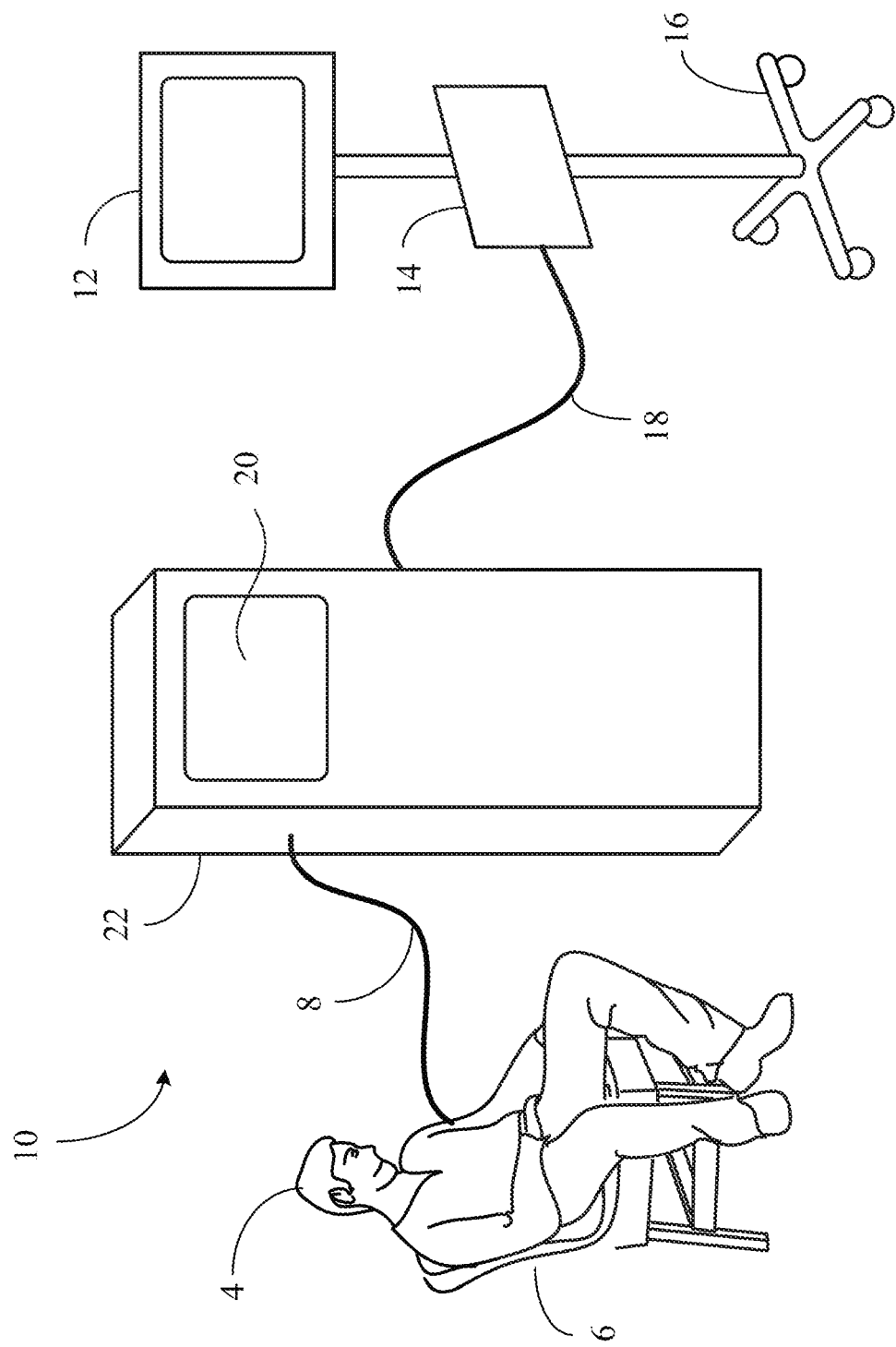
FIG. 1 is diagram showing an example of a patient care environment.

Hemodialysis is a process which employs a machine that includes a dialyzer to aid patients whose renal function has deteriorated to the point where their body cannot adequately rid itself of toxins. The dialyzer typically includes a semi-permeable membrane that serves to divide the dialyzer into two chambers. Blood is pumped through one chamber and a dialysis solution through the second. As the blood flows by the dialysis fluid, impurities, such as urea and creatinine, diffuse through the semi-permeable membrane into the dialysis solution. The electrolyte concentration of the dialysis fluid is set so as to maintain electrolytic balance within the patient.

Further purification in a dialyzer is possible through ultrafiltration. Ultrafiltration results from the normal situation wherein there is a positive pressure differential between the blood and the dialysis fluid chambers. This pressure differential causes water in the blood to pass through the membrane into the dialysis solution. This provides the benefit of reducing a dialysis patient's excess water load which normally would be eliminated through proper kidney functioning.

Patients undergoing dialysis therapy typically travel three or more times per week to hospital or dialysis centers that are designed for efficient and routine dialysis therapy. Hemodialysis is a complex treatment process in which, typically, an arterio-venous shunt, frequently termed a "fistula," is surgically inserted between a patient's artery and vein to facilitate transfer of blood from the patient to the dialyzer. During a normal dialysis treatment, one end of an arterial line or tube is inserted into the upstream end of the fistula (i.e., at a point near the patient's artery) and transports blood withdrawn from the upstream portion of the fistula to the inlet of the dialyzer. A venous line or tube is connected to the output of the blood side of the dialyzer returns treated blood to the fistula at an insertion point downstream of the arterial line (i.e., at a point near the patient's vein).

Successful dialysis treatment typically includes monitoring several patient vital signs and hemodialysis parameters during the dialysis process in order to optimize the overall efficacy of the dialysis procedure, to assess the condition of the fistula (the access to the patient's blood) and to determine the actual purification achieved. Some examples of parameters monitored and analyzed by a hemodialysis machine (or equipment include the blood access flow rate or the rate at which blood flows out of the patient to the dialyzer) and the ratio Kt/V to measure dialysis efficiency, where K is the clearance or dialysance (both terms representing the purification efficiency of the dialyzer), t is treatment time and V is the patient's total water value.

A processing device located on the hemodialysis machine may be used to manage and oversee the functions of the hemodialysis process and to, for example, monitor, analyze and interpret patient vital signs and hemodialysis parameters during a hemodialysis procedure. A health care practitioner such as a nurse, a patient care technician (or a home health aide if dialysis is performed at a patient's home) may oversee the dialysis treatment sessions. Data provided by the hemodialysis machine and the processing device may aid the health care practitioner in performing his or her duties.

Health care practitioners are often tasked with duties other than dialysis treatment oversight. For example, dialysis treatment centers must manage a large amount of data that must be entered and recorded. In addition to patient blood pressure, pulse, and select treatment parameters, other data relating to the patient may be entered, tracked, and coordinated, such as patient identity information, scheduling information, and billing information. Computing devices have been utilized to assist with data entry.

FIG. 1 shows an example of a patient care environment 10 in which a patient 4 seated in a chair 6 receives medical treatment from a treatment station 22. The medical treatment is, for example, dialysis, and, more particularly, hemodialysis. The treatment station 22 may be a hemodialysis treatment station or hemodialysis device. A tube or arterial line 8 transports blood from the patient 4 to the hemodialysis device 22 and back again to the patient 4 after processing and treatment in the hemodialysis device 22. The hemodialysis device 22 with display 20 is connected via cabling 18 to a processor 14 which controls a touch screen display 12. The touch screen display 12 is mounted on a movable stand 16. The touch screen display 12 includes a touch screen that permits a health care practitioner (HCP) such as a nurse, a patient care technician (or a home health aide if dialysis is performed at a patient's home), or even a patient to press the display 12 to, for example, enter patient or other data.

Figure 2:
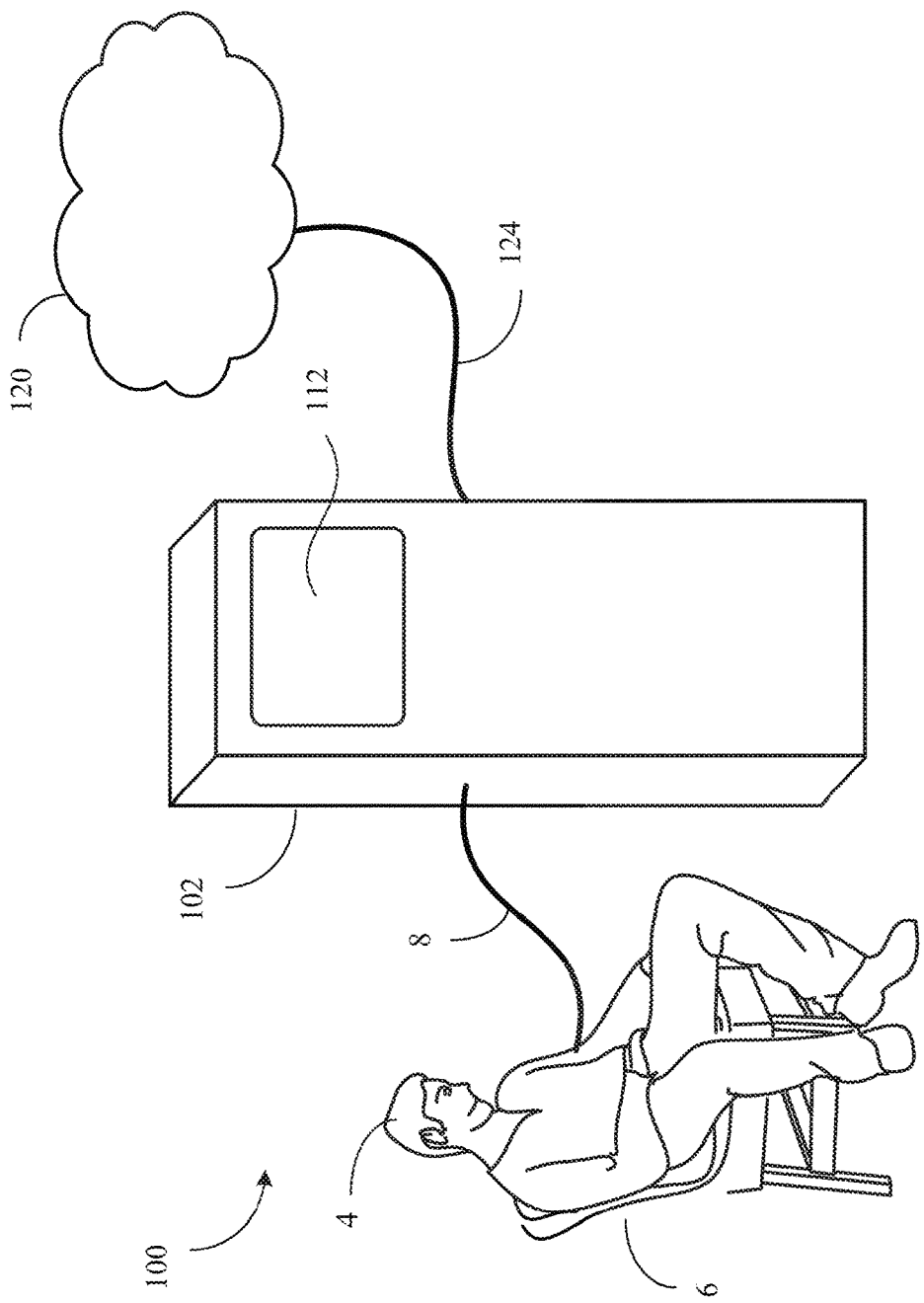
FIG. 2 is a diagram showing another example of a patient care environment.

FIG. 2 is a diagram of a patient care environment 100 in which the patient 4 is seated in the chair 6 and receives medical treatment from a treatment station 102. The treatment station 102 may be any medical device, for example, a dialysis device. Most particularly, the treatment station 102 may be a hemodialysis treatment station or hemodialysis device. The tube or arterial line 8 is, once again, used for transporting blood from the patient 4 to the hemodialysis (HD) device 102 and back again to the patient 4 after processing and treatment of the blood in the HD device 102. The HD device 102 may be configured to communicate with an external network 120, such as a local-area network or the Internet, via a wired or wireless connection 124.

The HD device 102 may include a display 112 with, e.g., touch screen or other user input features, such as a keyboard or touchpad. The HD device 102 may centralize and consolidate hemodialysis functions and data entry functions in a single device 102, without, e.g., the use of a separate, external display (e.g., display 12 of FIG. 1) or a separate, external processor (e.g., processor 14) with associated equipment (e.g., movable stand 16). Consolidation of functions in a single HD device 102 may also reduce the amount of external cabling (e.g., cabling 18) to the device 102. The HD device 102 may reduce the amount of space needed for hemodialysis treatment and present less crowding of the patient care environment 100. An HCP may be able to focus solely on the HD device 102, or the display 112 of the HD device 102, without the HCP's attention being diverted to, e.g., another external display. The HD device 102 may reduce power consumption and cost as compared to other, non-centralized implementations.

Due to the complex and precise nature of the hemodialysis process, hemodialysis functions, such as monitoring a patient's vital signs and monitoring the operation of hemodialysis machines are, in general, more critical to the safety and well-being of the patient 4 connected to the HD device 102 than other functions, such as patient data entry, that may be performed using the device 102. In the event that functions other than hemodialysis functions, such as providing medical records or communication programs, are to be integrated into the HD device 102, isolation of these functions from the hemodialysis functions may be achieved through the use of more than one processing device.

Use of more than one processing device may present its own set of design challenges since different processing devices used for different functions may be incompatible with one another and may communicate with, e.g., user interface devices (not shown in FIG. 2) in different, incompatible ways.

Figure 3:
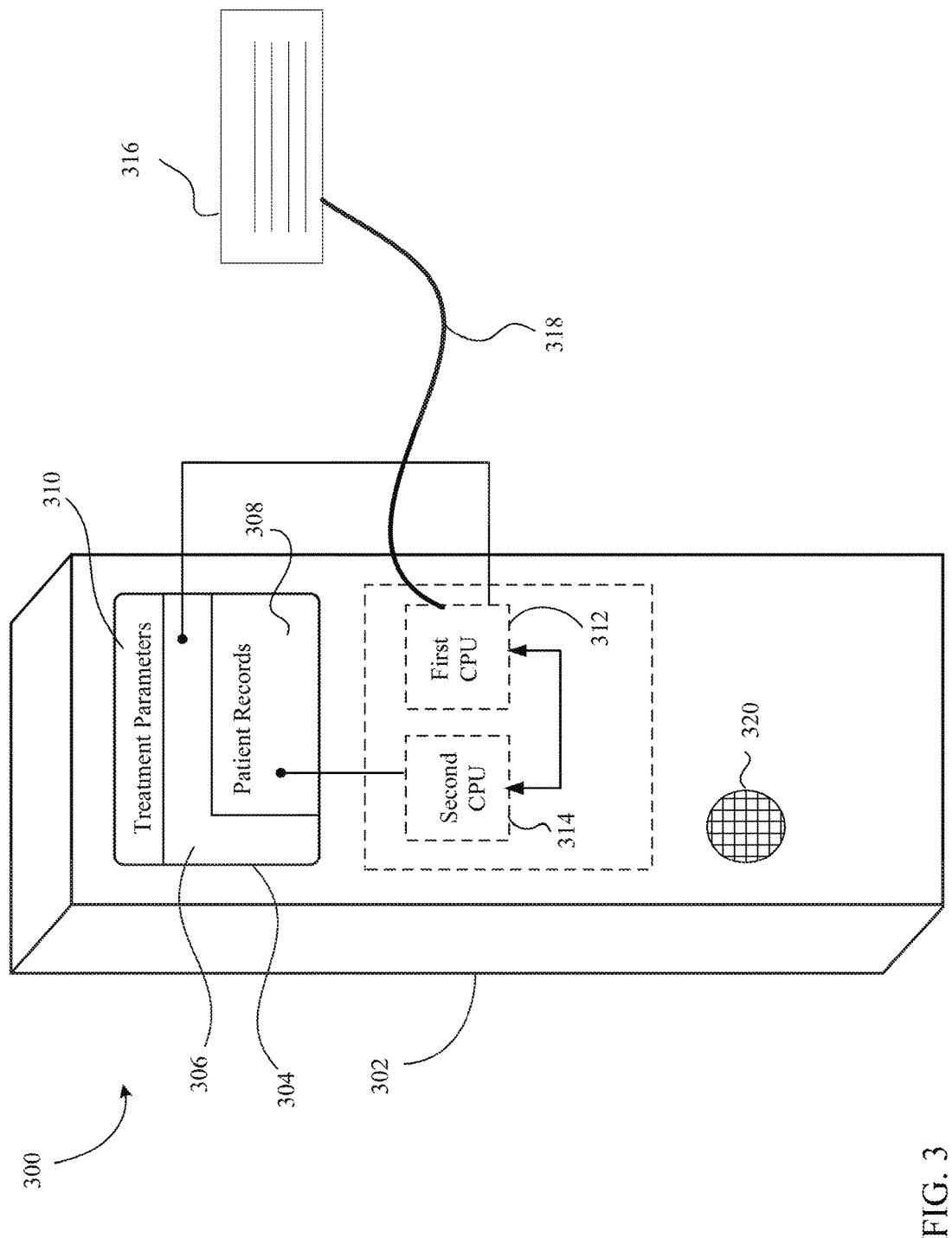
FIG. 3 is a diagram of an example hemodialysis machine.

FIG. 3 shows a medical treatment system 300 that includes a dialysis machine 302. The dialysis machine 302 may be configured to share user interface resources, (e.g., a user interface device 316) between a first processing device 312 and a second processing device 314. In some examples, the first and the second processing devices 312, 314 are configured to share the use of a display 304 associated with the dialysis machine 302. Although one user interface device 316 is shown in FIG. 3, several user interface devices may be used in the medical treatment system 300. While in the example of FIG. 3, the user interface device 316 is connected to the dialysis machine 302 via a cable 318, the user interface device 316 or other user interface devices can communicate wirelessly with the dialysis machine 302, or may be integral to the dialysis machine 302. In some cases, the display 304 of the dialysis machine 302 is used as the user interface.

The user interface devices used in medical treatment system 300 may include any of a variety of user interface devices known in the art, such as an alphanumeric keyboard or a keypad, a pointing device (e.g., a touchpad, a mouse, or a trackball), a display, and a display with a touch screen. In some examples, such as the example of FIG. 3, one or more of the user interface devices may be located external to the dialysis machine 302.

The first processing device 312 may be a functional dialysis processing device (FHP) that may be configured to monitor dialysis functions of the dialysis machine 302. The second processing device 314 may be a microprocessor, such as a standard personal computer (PC) processor, embedded within the dialysis machine 302, and may be referred to as an embedded processing device (EP). The second processing device 314 of the dialysis machine 302 may be configured to communicate with the external network 120 (FIG. 2), such as a local-area network or the Internet, via a wired or wireless connection 124 (FIG. 2) (and, e.g., via a network interface (not shown)). In FIG. 3, the second processing device 314 communicates with the user interface device 316 through the first processing device 312; however, the user interface device 316 or other user interface devices may communicate directly with the second processing device 314. Furthermore, while both the first processing device 312 and the second processing device 314 are shown as controlling (e.g., communicating directly with) the display 304, either or both of the first and second processing devices 312, 314 could communicate with the display 304 via one or more additional computing elements, such as one or more graphical processing units.

In some examples, the display 304 may include multiple display regions. For example, in FIG. 3, the display 304 includes both a first display region 306 and a second display region 308. The display 304 is configured to display the first and second display region one at a time (e.g., by toggling between the first display region 306 and the second display region 308), and to display the first display region 306 and the second display region 308 simultaneously, as shown. By way of example, one or both of the first display region 306 and the second display region 308 can be presented on the display 304 as one or more viewing panes. Thus, as illustrated in FIG. 3, the display 304 may simultaneously present a first display region 306 that is under the control of the first processing device 312 and a second display region 308 that is under the control of the second processing device 314. The first display region 306 may be configured to display information associated with the medical treatment of a patient, and the second display region 308 may be configured to display information associated with programs or processes running on the second processing device 314, such as medical database programs, communication programs (email clients, instant messaging programs), media players, and other programs or processes not directly related to the treatment of a dialysis patient.

At a given time during the operation of the dialysis machine 302, only one of the first display region 306 and the second display region 308 is active. In some examples, a display region can be said to be active when it may respond to user input (e.g., via the user input device 316). A display region can be made active automatically in response to an event, such as an alarm or notification associated with the medical treatment of a patient. A display region can also be made active in response to user activation of a control. For example, a user can use activate a portion of the first display region 306 with a cursor controlled by the user input device 316 in order to make the first display region 306 the active display region. In some examples, the dialysis machine 302 can automatically designate either the first display region 306 or the second display region 308 as the active display region. For example, if an alarm or notification is generated by the dialysis machine 302 in the first display region 306, the dialysis machine 302 can automatically designate the first display region 306 as the active display region of the display 304.

The arrangement of the first and second display regions can be altered according to user input or can be altered according to predefined rules (e.g., the execution of a particular program or programs can cause the arrangement of the first and second display regions to be altered).

In some examples, the first display region 306 includes a priority region 310 that, in some examples, is configured to always be displayed on the display 304 regardless of whether the first display region 306 is active. The priority region 310 is configured to display treatment parameters associated with the medical treatment of a patient, such as vital signs and dialysis parameters. The priority region 310 can alternatively be configured to present other important information, such as alarms and notifications associated with the medical treatment of a patient.

In some examples the priority region 310 of the first display region 306 cannot be obscured by other display regions, such as the second display region 308. For example, while the first and second display regions 306, 308 may be dragged, re-sized, and otherwise repositioned, the dialysis machine 302 can implement rules that prevent the second display region 308 from being positioned to overlap or cover the priority region 310.

The dialysis machine 302 also includes an audio device 320 which, in this example, is a speaker. The audio device 320 can provide an auditory cue that represents a notification or alarm. The auditory cue can be a voice message, a siren, or other sounds that are intended to attract attention or provide instructions.

Figure 4:
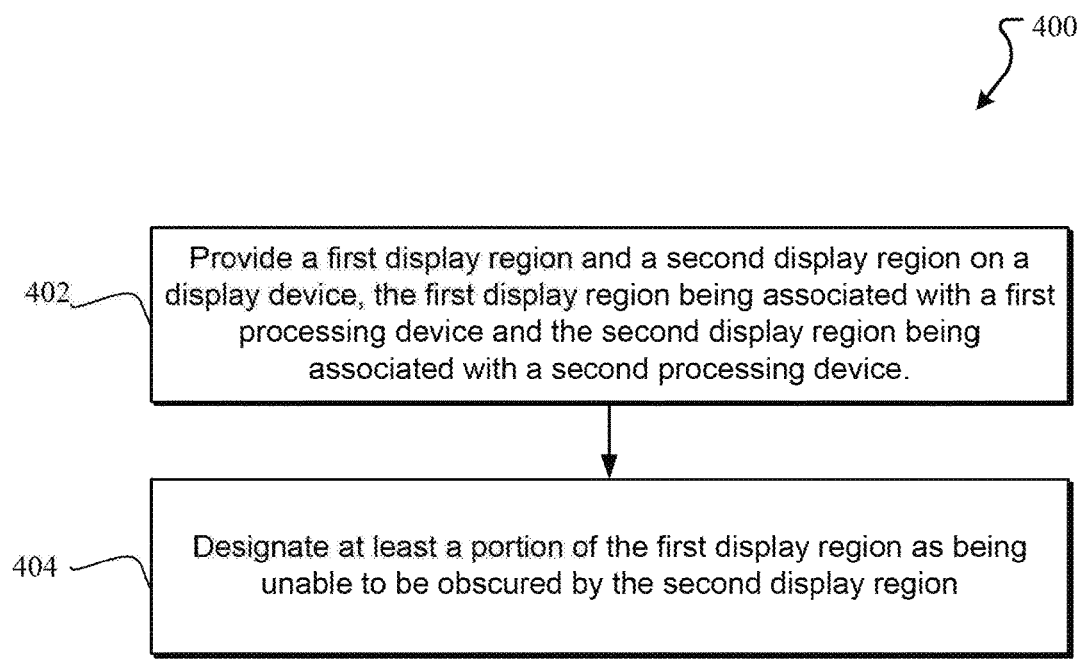
FIG. 4 illustrates an example process for displaying information.

FIG. 4 illustrates an example process 400 for presenting information on a display associated with a dialysis machine (e.g., the dialysis machine 302 (FIG. 3)). A first display region and a second display region is provided on a display device, the first display region being associated with a first processing device and the second display region being associated with a second processing device (402). In some examples, as shown in FIG. 3, the first display region and the second display region may be represented by respective viewing panes on a display, such as a liquid crystal display (LCD) embedded in the dialysis machine. In some examples, the first display region is associated with a first processing device that controls the main functions of the dialysis machine, such as the administration of treatment sessions. Similarly, the second display region may be associated with a second processing device that implements processes and/or programs that are ancillary to the medical treatment of a patient. For example, the second display region may display information associated with programs that manage patient medical records.

At least a portion of the first display region is designated as being unable to be obscured by the second display region (404). In some examples, the dialysis machine may designate a display region (or a portion thereof) as a region that is always visible on the display while the display is in operation. In other words, a display region that is designated as being unable to be obscured by a second display region can be said to be designated as a "priority" display region. In some examples, the dialysis machine designates a portion of a display region associated with the medical treatment of a patient as a display region that cannot be obscured by the second display region (or, in some examples, by any other display region). The dialysis machine can enforce rules that prevent the priority region from being obscured. For example, the dialysis machine can block display regions that are dragged toward the priority region in a way that prevents the priority region from being overlapped by another display region. In some examples, the priority region can be designated as having an "always on top" characteristic; for example, display regions that are dragged into a position that would otherwise overlap the priority display region can be shifted to a layer behind the priority display region (e.g., the dragged region would appear on the display as being behind the priority display region).

Figure 5:
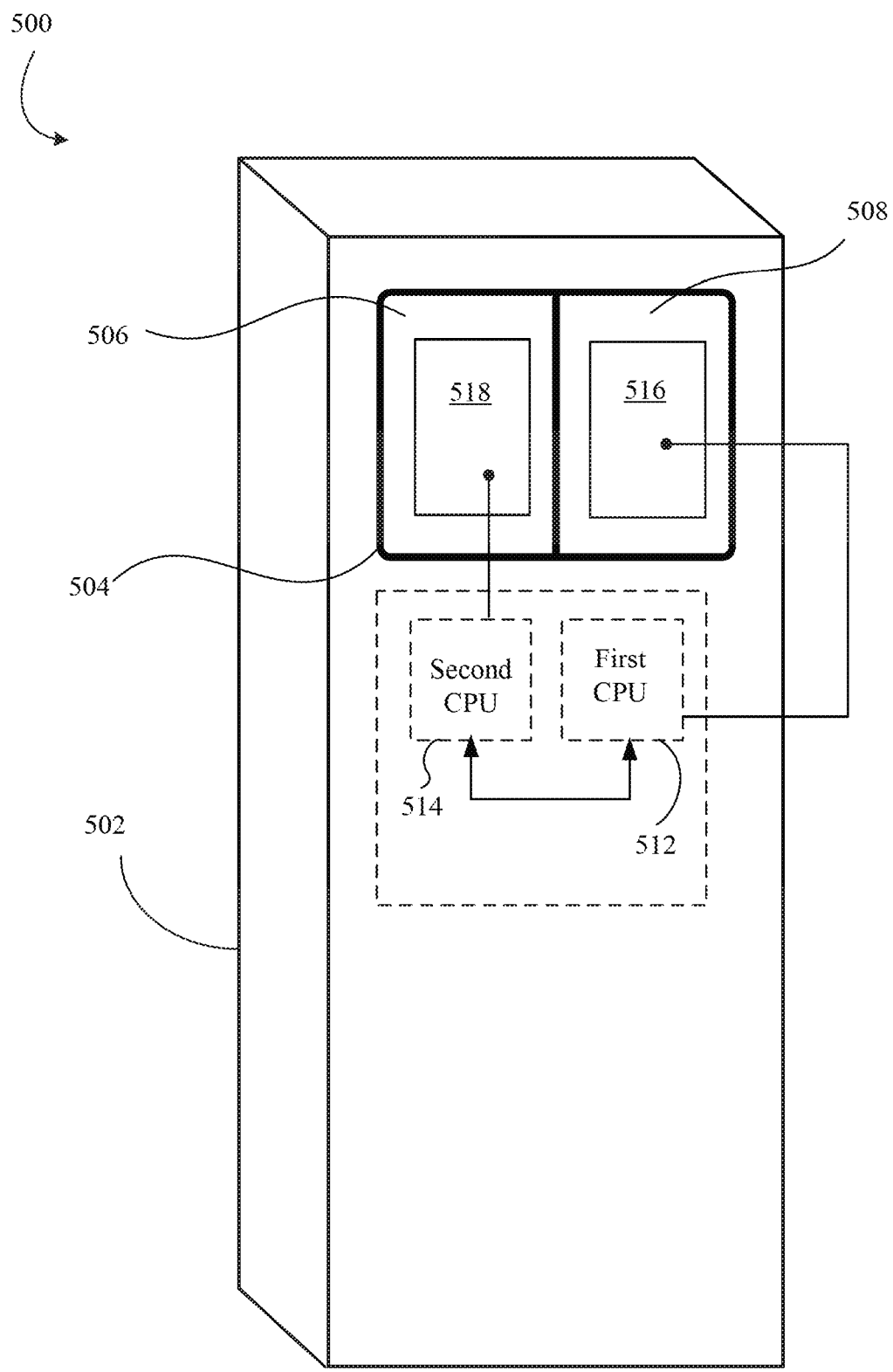
FIG. 5 is a diagram of an example hemodialysis machine.

FIG. 5 shows an example medical device system 500 that includes a dialysis machine 502. Like the dialysis machine 302 shown in FIG. 3, the dialysis machine 502 includes a display 504 that is configured to display both a first display region 516 and a second display region 518. In some examples, the first display region 516 is controlled by a first processing device 512, and the second display region 518 is controlled by a second processing device 514. In some examples, the first display region is associated with a first processing device that controls the main functions of the dialysis machine, such as the administration of treatment sessions. Similarly, the second display region may be associated with a second processing device that implements processes and/or programs that are ancillary to the medical treatment of a patient. For example, the second display region may display information associated with programs that manage patient medical records.

The display 504 of the dialysis machine 502 includes both a first dedicated display region 506 and a second dedicated display region 508. The first and second dedicated display regions 506, 508 may be dedicated portions of one physical display device, or may be comprised of two separate display devices (e.g., multiple LCD screens). In some examples, the dedicated display regions 506, 508 represent defined areas in which display regions are presented. For example, in FIG. 5, the first display region 516 and the second display region 518 are presented side-by-side in their corresponding dedicated display regions 506, 508. While the dedicated display regions 506, 508 are arranged side-by-side in FIG. 5, the dedicated display regions can be arranged in other configurations, such as a stacked configuration. Though only two dedicated display regions are shown, the dialysis machine 502 can include any number of dedicated display regions. The arrangement of dedicated display regions can be pre-defined (e.g., configured by a manufacturer of the dialysis machine 502) or can be defined by a user. The arrangement of the dedicated display regions can further be altered according to user input or can be altered according to predefined rules (e.g., the execution of a particular program or programs can cause the arrangement of the dedicated displays to be altered).

While the dialysis machines described above have been described as including two processing devices, the dialysis machines could include any number of processing devices. Similarly, while the dialysis machines described include either two display regions, two dedicated display regions, or both, dialysis machines can include any number of display regions or dedicated display regions. For example, a dialysis machine could include three dedicated display regions that each include four display regions (e.g., four viewing panes). Each viewing pane could be associated with a different processor, or multiple viewing panes could be associated with a single processor. Multiple display regions can relate to dialysis treatment, parameters, and alarms, and multiple display regions can relate to the presentation of information such as medical records and other information that may or may not be related to dialysis treatment.

In some examples, the first processing device may be configured to accept signals from one or more external sources of visual data (e.g., via one or more ports, such as universal serial bus (USB) ports (not shown)). For example, the first processing device may receive signals from an external display device (e.g., a "video-out" signal from an external LCD screen) that represent that images displayed on the external data source. The first processing device may then cause the data received from the external data source to be displayed on the display of the dialysis machine as a display region (e.g., a viewing pane) that represents the external data. Like a second display region associated with the second processing device 314 (FIG. 3), a display region associated with the external data source shares user input device(s) with the first processing device.

In some examples, the first processing device and the second processing device may communicate with one or more user interface devices via a third processing device. In some examples, the third processing device is a user interface processing (UIP) device that is associated with the dialysis machine. A UIP used in dialysis machines is described, for example, in U.S. patent application Ser. No. 12/137,375 ("the '375 application"), which is incorporated herein by reference in its entirety. As described in the '375 application, the UIP may "switch focus" between a first processing device (e.g., a main processing device) to a second processing device (e.g., a processing device associated with ancillary processes and programs). When the first processing device has focus, user input devices connected to the first processing device via the UIP will generally affect operation of the first processing device. When the second processing device has focus, the user input devices connected to second processing device via the UIP will generally affect operation of the second processing device. User interactions with the user input devices will likewise generally affect operation of whichever processing device has focus. The processing device that has focus may control a display associated with the dialysis machine in certain circumstances. In some examples, the processing device that has focus is represented by a display region (e.g., a viewing pane) that is in the active state. Switching focus, in this example, could designate a second display region as the active display region (e.g., clicking a non-active viewing pane could switch the focus of the UIP, resulting in the designation of the non-active viewing pane as an active viewing pane).

Although the processes described herein have been discussed in terms of dialysis machines such as hemodialysis and peritoneal dialysis machines, the processes described herein could, alternatively or additionally, be used in, and applied to, other medical devices.

In general, when a user interface device is said to control or affect operation of a processing device, it is understood that user interactions with a user interface device may cause a processing device (e.g., the first or second processing devices, or a user interface processing device) to control or affect such operation and thus the interactions themselves may also be said to control or affect such operation.

Connections may be wired and/or wireless connections. When one component is said to be connected to another component, the component may be directly connected or indirectly connected (via, e.g., still another component) to the other component.

The processes described herein and their various modifications (hereinafter "the processes"), are not limited to the hardware and software described above. All or part of the processes can be implemented, at least in part, via a computer program product, e.g., a computer program tangibly embodied in an information carrier, such as one or more machine-readable media or a propagated signal, for execution by, or to control the operation of, one or more data processing apparatus, e.g., a programmable processor, a computer, multiple computers, and/or programmable logic components.

A computer program can be written in any form of programming language, including compiled or interpreted languages, and it can be deployed in any form, including as a stand-alone program or as a module, component, subrouting, or other unit suitable for use in a computing environment. A computer program can be deployed to be executed on one computer or on multiple computers at one site or distributed across multiple sites and interconnected by a network.

Actions associated with implementing all or part of the processes can be performed by one or more programmable processing devices executing one or more computer programs to perform the functions of the processes. All or part of the processes can be implemented as, special purpose logic circuitry, e.g., an FPGA (field programmable gate array), an ASIC (application-specific integrated circuit), and/or a CPLP (complex programmable logic device).

Processing devices suitable for the execution of a computer program include, by way of example, both general and special purpose microprocessors, and any one or more processors of any kind of digital computer. Generally, a processing device will receive instructions and data from a read-only memory or a random access memory or both. Components of a computer include one or more processing devices for executing instructions and one or more memory devices for storing instructions and data.

Components of different implementations described herein may be combined to form implementations not specifically set forth above. Other implementations not specifically described are also within the scope of the following claims.

What is claimed is:

1. A dialysis system comprising:
   a dialysis machine;
   one or more processing devices;
   a display device; and
   memory configured to store instructions that, when executed, cause the display device to:
      provide a first display region and a second display region, the first display region being associated with at least one of the one or more processing devices and the second display region being associated with at least one of the one or more processing devices, and
      designate either the first display region or the second display region as an active display region,
   wherein the display device is configured to:
      automatically designate the first display region as the active display region in response to one or more notifications or alarms associated with a dialysis treatment session being displayed in the first display region, or
      automatically designate the second display region as the active display region in response to one or more notifications or alarms being displayed in the second display region,
   wherein the active display region is able to respond to user input while in an active state, and the other, inactive display region is not able to respond to user input while in an inactive state.

2. The dialysis system of claim 1, wherein the display device is configured to present information related to the dialysis treatment session in the first display region.

3. The dialysis system of claim 2, wherein the information related to the dialysis treatment session includes information corresponding to one or both of patient vital signs during the dialysis treatment session and dialysis parameters during the dialysis treatment session.

4. The dialysis system of claim 3, wherein the corresponding information includes information related to one or more of a purification achieved by the dialysis treatment session, an efficiency of the dialysis treatment session, and a rate at which blood flows out of a patient undergoing the dialysis treatment session.

5. The dialysis system of claim 1, wherein the display device is configured to wirelessly communicate with the dialysis machine and the one or more processing devices.

6. The dialysis system of claim 1, wherein the display device is configured to present information related to one or more medical records in the second display region.

7. The dialysis system of claim 1, wherein the display device is configured to present information that is not directly related to the dialysis treatment session in the second display region.

8. The dialysis system of claim 7, wherein the display device is configured to present information related to one or more of medical database programs, communication programs, and a media player.

9. The dialysis system of claim 1, wherein the one or more processing devices are configured to wirelessly communicate with a network.

10. The dialysis system of claim 9, wherein the network includes a medical database, and the display device is configured to present information related to one or more medical records of a patient undergoing the dialysis treatment session.

11. The dialysis system of claim 1, wherein the display device is configured to receive user input.

12. The dialysis system of claim 11, wherein the user input is used to control dialysis functions of the dialysis machine during the dialysis treatment session.

13. The dialysis system of claim 12, wherein the dialysis functions include one or more of infusing, dwelling, and draining dialysate to and from a patient's peritoneal cavity.

14. The dialysis system of claim 12, wherein information related to the user input is wirelessly transmitted to the dialysis machine.

15. The dialysis system of claim 12, wherein the dialysis functions include one or both of pumping blood of a patient through a blood chamber of the dialysis machine and pumping a dialysis solution through a dialysis fluid chamber of the dialysis machine.

16. The dialysis system of claim 15, wherein the dialysis functions include one or both of altering a pressure in the blood chamber and altering a pressure in the dialysis fluid chamber.

17. The dialysis system of claim 11, wherein the active display region is responsive to the user input and the other display region is not responsive to the user input.

18. The dialysis system of claim 11, wherein the user input is used to designate either the first display region or the second display region as the active display region.

19. The dialysis system of claim 11, wherein an arrangement of one or both of the first display region and the second display region is altered according to the user input.

20. The dialysis system of claim 11, wherein the user input is used for data entry functions.

21. The dialysis system of claim 1, wherein one of the one or more processing devices is integral to the dialysis machine.

22. The dialysis system of claim 1, wherein one of the one or more processing devices performs functions isolated from dialysis functions of the dialysis machine.

23. The dialysis system of claim 1, wherein the display device is integral to the dialysis machine.

24. The dialysis system of claim 1, comprising a user interface device configured to wirelessly provide control signals to the dialysis machine for controlling dialysis functions during the dialysis treatment session.

25. A method comprising:
providing, on a display device associated with a dialysis machine, a first display region and a second display region, the first display region being associated with at least one of one or more processing devices of the dialysis machine and the second display region being associated with at least one of the one or more processing devices; and
designating either the first display region or the second display region as an active display region,
wherein the display device is configured to:
automatically designate the first display region as the active display region in response to one or more notifications or alarms associated with a dialysis treatment session being displayed in the first display region, or
automatically designate the second display region as the active display region in response to one or more notifications or alarms being displayed in the second display region,
wherein the active display region is able to respond to user input while in an active state, and the other, inactive display region is not able to respond to user input while in an inactive state.

26. The method of claim 25, wherein the display device is configured to wirelessly communicate with the dialysis machine and the one or more processing devices.

27. A method of providing dialysis treatment comprising:
providing, on a display device associated with a dialysis machine during dialysis treatment of a patient, a first display region and a second display region, the first display region being associated with at least one of one or more processing devices of the dialysis machine and the second display region being associated with at least one of the one or more processing devices; and
designating either the first display region or the second display region as an active display region,
wherein the display device is configured to:
automatically designate the first display region as the active display region in response to one or more notifications or alarms associated with the dialysis treatment being displayed in the first display region, or
automatically designate the second display region as the active display region in response to one or more notifications or alarms being displayed in the second display region,
wherein the active display region is able to respond to user input while in an active state, and the other, inactive display region is not able to respond to user input while in an inactive state, and
wherein the display device is configured to present information related to the dialysis treatment in the first display region and information related to one or more medical records associated with the patient in the second display region.

28. The method of claim 27, wherein the display device is configured to wirelessly communicate with the dialysis machine and the one or more processing devices.

29. A user interface device configured to wirelessly communicate with a dialysis machine, comprising:
a display;
a user interface processor configured to control the display; and
memory configured to store instructions that, when executed by the user interface processor, cause the display to:
provide a first display region and a second display region, the first display region being associated with at least one of one or more processing devices of the dialysis machine and the second display region being associated with at least one of the one or more processing devices, wherein at least one of the one or more processing devices is configured to monitor dialysis functions of the dialysis machine; and
designate either the first display region or the second display region as an active display region;
wherein the display is configured to:
automatically designate the first display region as the active display region in response to one or more notifications or alarms associated with a dialysis treatment being displayed in the first display region, or
automatically designate the second display region as the active display region in response to one or more notifications or alarms being displayed in the second display region, wherein the active display region is able to respond to user input while in an active state, and the other, inactive display region is not able to respond to user input while in an inactive state.

30. The user interface device of claim 29, wherein the user interface device is configured to wirelessly communicate with the one or more processing devices via the user interface processor.

31. The user interface device of claim 29, wherein the user interface device is configured to:
  receive user input; and
  wirelessly provide control signals to the dialysis machine for controlling dialysis functions based on the user input.

* * * * *